US006813951B2

United States Patent
Blouin et al.

(10) Patent No.: US 6,813,951 B2
(45) Date of Patent: Nov. 9, 2004

(54) LASER-ULTRASONIC TESTING SYSTEM

(75) Inventors: Alain Blouin, Montreal (CA); Lionel Pujol, Sainte-Foy (CA); Jean-Pierre Monchalin, Montreal (CA)

(73) Assignee: National Research Council of Canada, Ottawa (CA)

( * ) Notice: Subject to any disclaimer, the term of this patent is extended or adjusted under 35 U.S.C. 154(b) by 50 days.

(21) Appl. No.: 10/332,804

(22) PCT Filed: Jul. 10, 2001

(86) PCT No.: PCT/CA01/01005

§ 371 (c)(1),
(2), (4) Date: May 14, 2003

(87) PCT Pub. No.: WO02/06813

PCT Pub. Date: Jan. 24, 2002

(65) Prior Publication Data

US 2003/0172736 A1 Sep. 18, 2003

Related U.S. Application Data

(60) Provisional application No. 60/218,046, filed on Jul. 13, 2000.

(51) Int. Cl.[7] .............................................. G01N 29/00
(52) U.S. Cl. .............................. 73/643; 73/655; 73/657
(58) Field of Search ........................ 73/643, 655, 657, 73/159, 601, 646; 356/450, 461, 480; 372/92

(56) References Cited

U.S. PATENT DOCUMENTS

| | | | | |
|---|---|---|---|---|
| 4,966,459 A | * | 10/1990 | Monchalin | 356/502 |
| 5,131,748 A | * | 7/1992 | Monchalin et al. | 356/486 |
| 5,479,431 A | * | 12/1995 | Sobottke et al. | 372/92 |
| 5,608,166 A | | 3/1997 | Monchalin et al. | 73/657 |
| 5,854,802 A | * | 12/1998 | Jin et al. | 372/22 |
| 6,122,060 A | * | 9/2000 | Drake, Jr. | 356/511 |
| 6,335,943 B1 | * | 1/2002 | Lorraine et al. | 372/28 |
| 6,483,859 B1 | * | 11/2002 | Drake, Jr. | 372/25 |
| 6,543,288 B1 | * | 4/2003 | Blouin et al. | 73/643 |
| 6,608,848 B2 | * | 8/2003 | Kleinschmidt et al. | 372/32 |

FOREIGN PATENT DOCUMENTS

| | | |
|---|---|---|
| EP | 0 702 230 A2 | 3/1996 |
| WO | WO 98/22801 | 5/1998 |

* cited by examiner

*Primary Examiner*—Hezron Williams
*Assistant Examiner*—Jacques M. Saint-Surin
(74) *Attorney, Agent, or Firm*—Marks & Clerk

(57) ABSTRACT

In a method for ultrasonic testing of objects, ultrasound is generated inside or at the surface of the object. The surface of the object is illuminated with a beam from a long-pulse laser oscillator, typically in the range 1 µs to a few 100 µs, that is substantially free of intensity fluctuations. The light from the incident beam that is scattered or reflected by the surface of the object is collected and demodulated to obtain a signal representative of the ultrasonic motion. The method allows for the use of a compact and efficient arrangement.

37 Claims, 6 Drawing Sheets

LASER-ULTRASONIC TESTING SYSTEM

CROSS REFERENCE TO RELATED APPLICATION

This application claims the benefit under 35 USC 119(e) of U.S. Provisional Application No. 60/218,046 filed Jul. 13, 2000.

BACKGROUND OF THE INVENTION

1. Field of the Invention

This invention relates to the field of materials testing, and in particular to a laser-ultrasonic system for the ultrasonic testing of objects or characterizing of materials with ultrasound.

2. Description of Related Art

Figure 1:
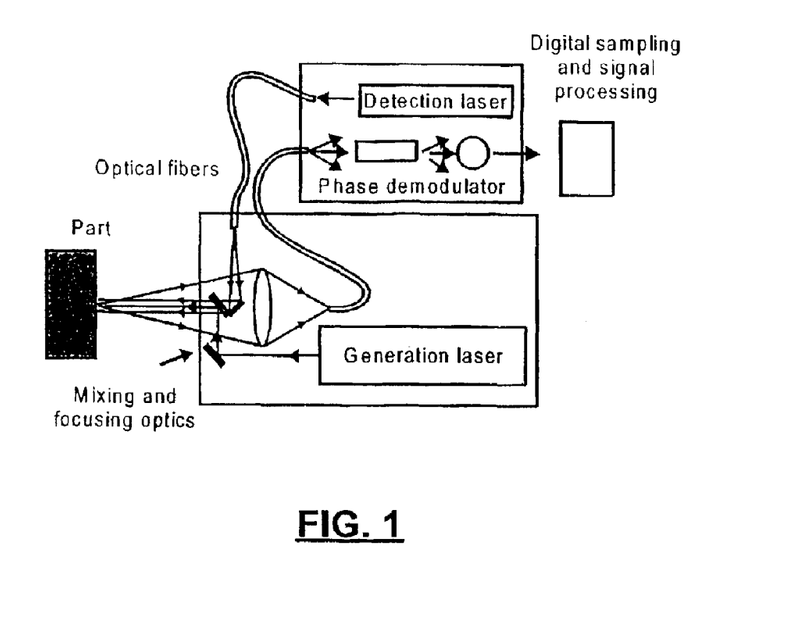
FIG. 1 is a schematic view of a prior art laser-ultrasonic inspection system.

Laser-ultrasonics is an emerging technique for the nondestructive evaluation of objects and materials, which has several advantages over other nondestructive techniques. A typical laser-ultrasonic inspection system is composed of two lasers and a phase or frequency demodulator, as shown in FIG. 1. In laser-ultrasonics, the generation of ultrasound is performed at a distance, which in practice can range from a fraction of a meter to several meters. The source of ultrasound is the surface of the material itself and detection of ultrasonic motion is performed off the same surface, which eliminates the coupling liquid and perpendicularity requirements of conventional ultrasonics.

Laser-ultrasonics can be used on parts of complex shape and at elevated temperatures. The laser-ultrasonic technology has been demonstrated to be applicable to real industrial conditions. In particular, a system has been developed for measuring on-line the wall thickness of steel tubes at 1000° C. moving at 4 m/s. Systems have also been developed for the inspection of aircraft parts with very complex geometries and made of composite materials. Many other applications are presently explored and have been presented in various conferences on ultrasonics, optics or non-destructive testing.

In order to be useful in practice laser-ultrasonics generally requires strong ultrasound generation and sensitive detection. Various techniques are known to improve generation strength and have been described in the literature. One technique consists in using material ablation. This has the disadvantage of causing some mate rial damage. Another technique involves using a laser with a wavelength that provides light penetration below the material surface.

Many interferometric detection schemes are known. Optical detection of ultrasound is based on the demodulation of the small phase or frequency shift imparted on the light from the detection laser scattered by the surface in ultrasonic motion. The detection schemes can be sensitive to the speckle of the scattered light (such as in U.S. Pat. No. 4,633,715 by J.-P. Monchalin entitled "Laser Heterodyne Interferometric Method and System for Measuring Ultrasonic Displacements") or insensitive to the speckle such as the scheme based on a confocal Fabry-Perot interferometer (U.S. Pat. No. 4,659,224 by J.-P. Monchalin, entitled *Optical Interferometric Reception of Ultrasonic Energy*, U.S. Pat. No. 4,966,459 by J.-P. Monchalin entitled *Broadband optical detection of transient surface motion from a scattering surface*, U.S. Pat. No. 5,137,361 by R. Héon and J.-P. Monchalin entitled *Optical detection of a surface motion of an object using a stabilized interferometric cavity* and U.S. Pat. No. 5,080,491 by J.-P. Monchalin and R. Héon entitled Laser optical ultrasound detection using two interferometer systems). Insensitivity to the speckles means that demodulation is insensitive to the wavefront of the scattered wave. In other words, demodulation occurs effectively on a large number of speckles (in contrast with the speckle sensitive schemes that work best with one speckle) and that the demodulator has a large etendue or throughput. These terms mean that the demodulator can effectively demodulate light coming from a large illuminated detection spot and received through a large aperture.

Insensitivity to speckle can also be realized by adaptation of the reference wave of the interferometer in a non-linear optical element, which is usually in practice a photorefractive crystal. A holographic grating is written inside the crystal by interference of the wave scattered by the surface and a pump wave directly derived from the detection laser. This grating then diffracts a reference wave with a wavefront adapted to the one of the received scattered wave. Such a scheme (two-wave mixing) is described in U.S. Pat. No. 5,131,748 by J.-P. Monchalin and R. K. Ing entitled *Broadband Optical Detection of Transient Motion from a Scattering Surface* and U.S. Pat. No. 5,680,212 by A. Blouin, P. Delaye, D. Drolet, J.-P. Monchalin, G. Roosen entitled *Sensitive and fast response optical detection of transient motion from a scattering surface by two-wave mixing*. This scheme provides also automatically frequency tracking to drifts or changes of frequency of the detection laser (within the response time of the two-wave mixing interferometer). It does not require a stabilization electrical network to lock the laser frequency to the interferometer as the confocal Fabry-Perot based detection schemes.

Other adaptive two-beam mixing demodulators also present similar properties of speckle insensitivity like the photo-emf based demodulator proposed by M. P. Petrov, I. A. Sokolov, S. I. Stepanov, G. S. Trofimov, *Non-steady-state photo-electromotive-force induced by dynamic gratings in partially compensated photoconductors* in J. Appl. Phys. 68, 2216, (1990) or more recently the demodulator based on the polarization self-modulation effect by K. Päivasaari, A. A. Kamshilin, *Adaptive sensors of rough-surface ultrasonic vibrations based on the polarization self-modulation effect*, Fourth International Conference on Vibration Measurements by Laser Techniques: Advances and Applications, SPIE Proceedings vol. 4072, 70, (2000).

In spite of these advances in speckle insensitive demodulation that make optical detection of ultrasound more practical for detection off industrial surfaces that are usually rough, they do not ensure that the technique is sufficiently sensitive, particularly when the ultrasonic signals are very weak (e.g. thick specimens and ultrasonically absorbing objects), when the surface is strongly absorbing light (e.g. all black carbon-epoxy composite materials) and when detection has to be performed meters away (e.g. objects at elevated temperature and inspection over large aircraft parts). In all these cases, in order to have adequate sensitivity the detection laser has to be powerful. Kilowatts peak power often gives only milliwatts at the interferometer level because of the many losses encountered when going from the laser to the demodulator. Such a power would be in practice hardly feasible if needed continuously; fortunately, it is only required from time to time at the repetition rate of ultrasound generation and over a time window in the range of 1 $\mu$s to a few 100 $\mu$s, depending upon the propagating time of ultrasound in the object or at its surface. However there are in addition severe stability criteria, in frequency or phase and intensity, since the laser should not introduce on the detector noise above the shot noise.

Current practice is to start from a very stable cw (continuous wave) low power (typically 100 mW) Nd-YAG laser oscillator and to amplify it to the desired peak power with several Nd-YAG pulsed amplifiers or using several passes in one amplifier or a combination of both. The amplifiers can be flashlamp pumped or laser diodes pumped. Nd-YAG and a few other materials are capable of providing the high gain needed. The cw low power laser oscillator is typically monolithic and pumped by a laser diode and has by design the stability requirements. A stabilization loop is often used to minimize the relaxation oscillations that appear in intensity and in phase, improving further stability.

Figure 2:
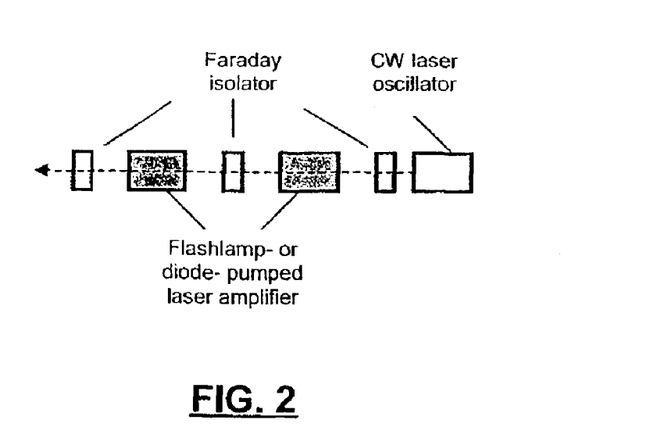
FIG. 2 is a schematic view of a prior art stable and powerful detection laser made by using a low power cw very stable laser oscillator followed by several rod amplifier stages. Each rod amplifier is usually double passed.
Figure 3:
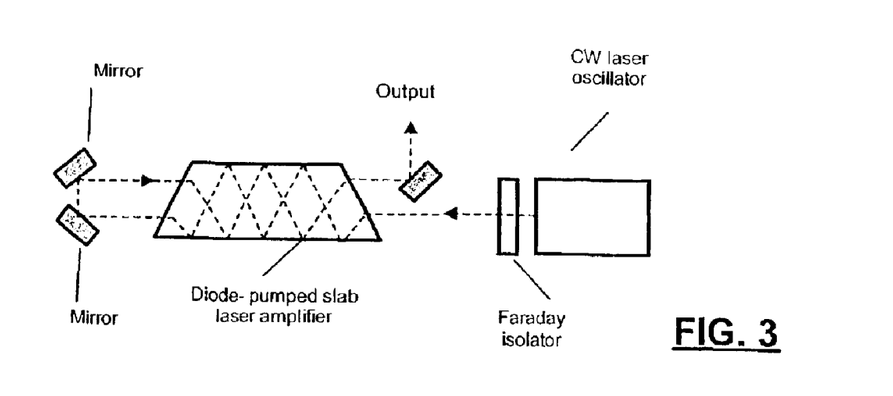
FIG. 3 is a schematic view of a prior art stable and powerful detection laser made by using a low power cw very stable laser oscillator followed by a laser slab amplifier which is multi passed. Only two passes are shown for the sake of clarity.

Commercial products are in particular available from Lightwave Electronics in California and InnoLight in Germany. Amplification maintains the stability properties of the low power cw laser oscillator, resulting in a high peak power output with the desired phase or frequency and intensity stability. A typical multi-amplification stage system is shown in FIG. 2. Each stage usually includes a laser rod (flashlamp pumped or laser diode pumped) and is doubled pass. Permanent magnet Faraday isolators are added between the cw laser oscillator, between stages and at the output to prevent parasitic oscillation (i.e. lasing) of the whole system. FIG. 3 shows a typical zig-zag multipass slab system. Such a system is usually laser diode pumped. Only two passes are shown for sake of clarity.

U.S. Pat. No. 5,608,166 describes the use of a long pulse detection laser, but this is not suitable for objects noted above that provide very weak ultrasonic signals and require a high power laser. Such high power lasers are too noisy to provide adequate sensitivity for very weak ultrasonic signals.

It is readily apparent that these existing detection laser systems are very complex, have a very large footprint and in turn have a high cost, which limits widespread use of the laser-ultrasonic technique. There is a need for a simpler, more compact and less costly detection system to be used concurrently with a suitable demodulator (preferably speckle insensitive).

SUMMARY OF THE INVENTION

According to the present invention there is provided a method for ultrasonic testing of objects comprising the steps of generating ultrasound inside or at the surface of the object; illuminating the surface of the object with an incident beam from a long-pulse laser oscillator that is modified to be substantially free of intensity fluctuations; collecting light from said beam that is scattered or reflected by the surface of the object; and demodulating the scattered light with a frequency tracking demodulator to obtain a signal representative of the ultrasonic motion.

A long pulse laser typically has a pulse duration in the range 1 μs to a few 100 μs. Long pulse lasers that provide the desired peak power with a pulse duration in the 100 μs range are known to be very noisy and are typically affected by strong relaxation oscillations and even spiking. The applicants have found surprisingly that if steps are taken to reduce intensity fluctuations if the proper demodulation is used, an effective solution to the problem is provided.

In a preferred embodiment, the long pulse laser oscillator is concurrently used with a speckle insensitive phase demodulator for the optical detection of ultrasound.

In another aspect the invention provides an apparatus for the ultrasonic testing of an object comprising an ultrasound generator for generating ultrasound inside or at the surface of the object; a Long pulse laser oscillator that is substantially free of intensity fluctuations for generating an incident beam for illuminating the surface of the object; a tight collector for collecting Light from said beam that is scattered or reflected by the surface of the object; and a frequency tracking demodulator for demodulating the collected tight to obtain a signal representative of the ultrasonic motion.

BRIEF DESCRIPTION OF THE DRAWINGS

The invention will now be described in more detail, by way of example only, with reference to the accompanying drawings, in which.

DETAILED DESCRIPTION OF THE PREFERRED EMBODIMENTS OF THE INVENTION

Figure 4:
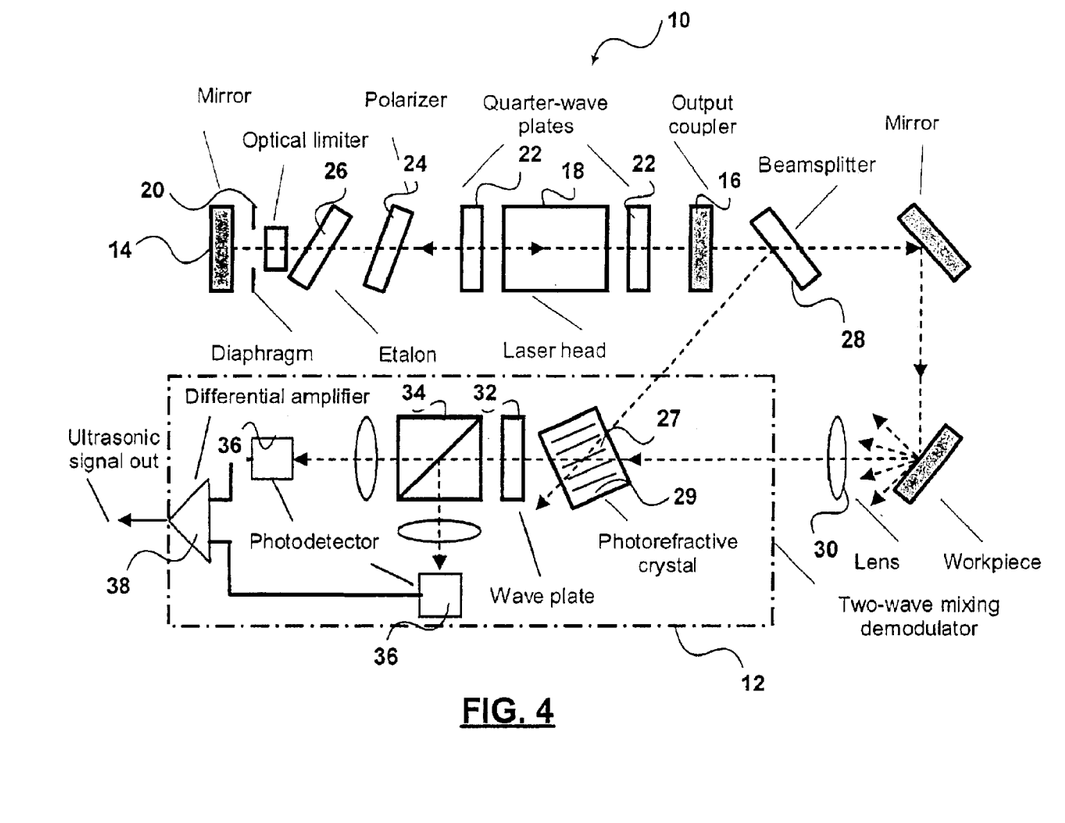
FIG. 4 is a schematic block diagram of a first embodiment of a detection system which includes a pulsed laser oscillator coupled to a two-wave mixing photorefractive demodulator.

The first embodiment of this invention is shown in FIG. 4. This embodiment is composed of a long pulse laser oscillator 10 and a two-wave mixing phase demodulator 12. The resonant cavity of the laser oscillator is composed of a mirror 14, an output coupler 16 and a laser bead 18, which contains the lasing medium and intra-cavity elements. The laser medium is preferably a solid-state laser medium, such as Nd-YAG, but gas or liquid can also be used. The solid-state laser medium has the shape of a rod, a disk or a slab, and is pumped by a flashlamp or laser diodes (the pumping means is not represented in FIG. 4).

Figure 5:
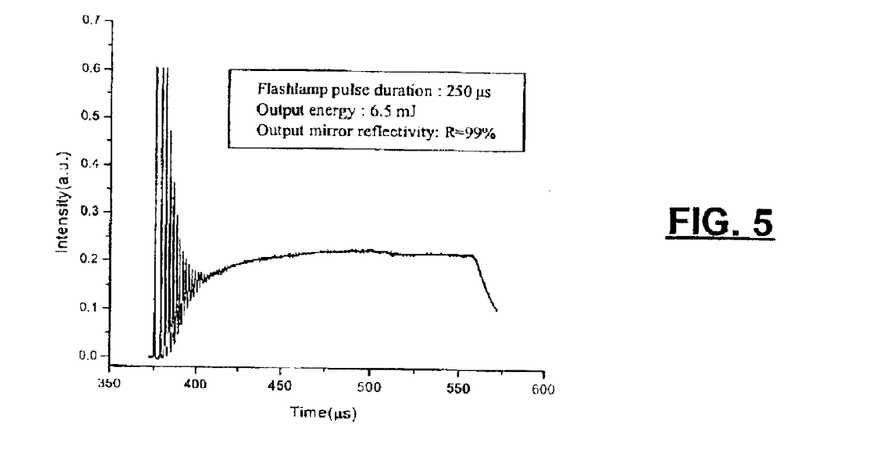
FIG. 5 shows the output of the laser oscillator operated in the multimode regime with a KTP frequency doubling crystal.

A diaphragm 20 is inserted in the laser cavity to select the fundamental $TEM_{00}$ laser cavity mode. Two quarter-wave plates 22, one on each side of the laser medium, are used to reduce the spatial hole burning, resulting in more competition between the modes that could oscillate and higher gain These two quarter-wave plates also act as a rough mode selector. A glass plate 24 at Brewster angle or a polarizer is also inserted in the cavity to force the laser to oscillate on a given linear polarization. The time duration of the pumping (flashlamp or laser diodes) excitation is chosen to be sufficiently long to let the intensity fluctuations damp out during the laser pulse. The laser has a strongly fluctuating output (spiking) followed by a much quieter period during which ultrasound could be detected. A typical result obtained for the laser output intensity without any longitudinal mode-selecting element in the cavity, i.e. in the case of multi longitudinal modes emission, is shown in FIG. 5. Often in order to have a long coherence length and to be able to operate with very unequal interferometer arms, the Laser oscillator is preferably operated in a single frequency mode.

Figure 6:
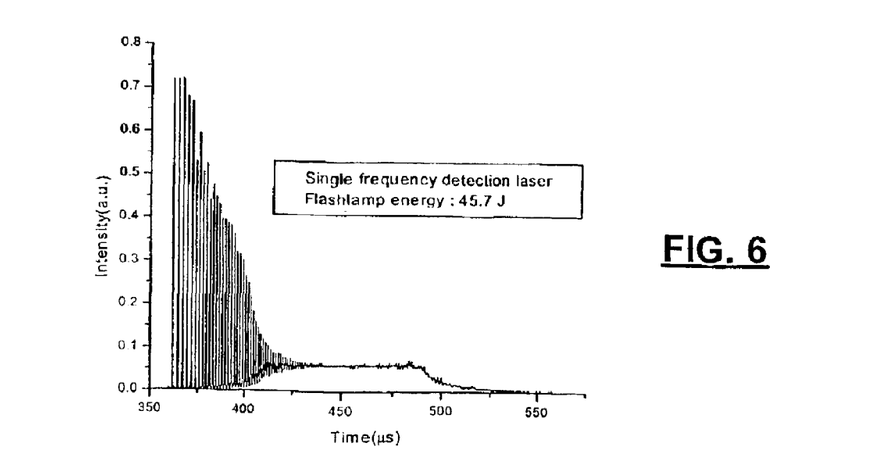
FIG. 6 shows the output of the laser oscillator operated in the single frequency mode with 45.7 J flashlamp pump energy.

As shown in FIG. 4, the single frequency regime is obtained by using one or two tilted etalons 26 in the cavity. This selection of one longitudinal mode can also be made by using a Lyot filter. An optical limiter 25 can also be inserted in the laser cavity to reduce further the decay time of the spiking or intensity modulation produced by the relaxation oscillations. Such an optical limiter 25 can be based on frequency doubling or higher harmonic generation or two-photon absorption in a selected medium, a GaAs crystal for the Nd:YAG wavelength for example. A typical result obtained with a frequency doubling nonlinear crystal used as the optical limiter in the cavity is shown in FIG. 6. The output peak power of the laser in the single frequency regime was about 40 Watts but a more powerful output can be obtained if a more powerful power supply had been used. Since the tilted etalon 26 introduces losses in the cavity, the laser power inside the cavity is smaller in the single frequency regime than in the multimode regime, which results in a slower decay time of the fluctuations.

Figure 7:
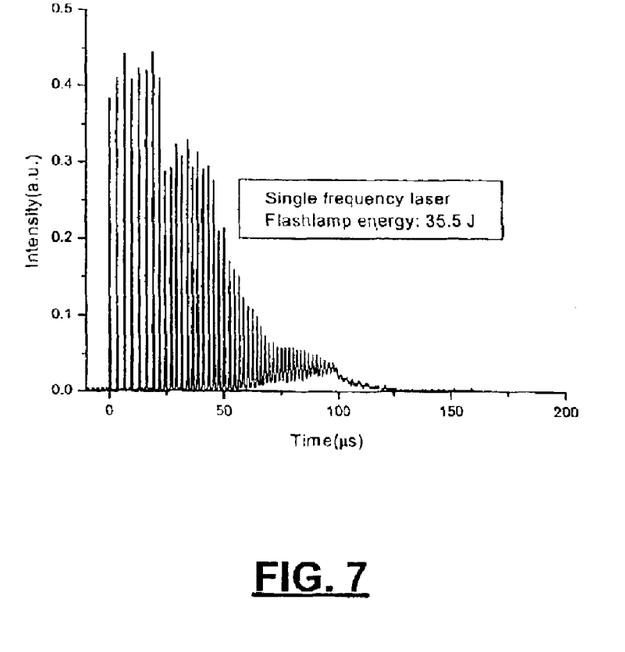
FIG. 7 shows the output of the laser oscillator operated in the single frequency mode with a 35.5 J flashlamp pump energy.

Reducing the strength of laser medium pumping has also the same effect, as shown by comparing FIGS. 6 and 7, the latter being obtained with a reduced energy provided to the flashlamp. Increasing the output coupling has also a similar effect. Hence, the laser cavity design is a trade-off between intracavity power and output power, while sufficiently strong and long pumping is key to get nearly noise free stable lasing. However in practice, the laser oscillator output has still some residual intensity fluctuations and its frequency is not stable, especially from laser shot to laser shot. Successful detection of ultrasound requires to use it use with a proper demodulator, which first tracks automatically the frequency drifts and second is not sensitive to intensity fluctuations. The described laser oscillator generates enough power, several ten or hundreds of watts typically, to be used in many laser-ultrasonic applications. However, if required, this laser oscillator can be followed by an optical amplifier to increase the available laser power to the kilowatt range.

A successful implementation of demodulation with the developed long pulse laser oscillator is shown in FIG. 4 and is based on the two-wave mixing detection scheme in a photorefractive crystal 27. As shown in FIG. 4, a beamsplitter 28 at the detection laser output is used to sample a fraction of the laser power for use as pump beam. The remaining power of the detection laser beam is then sent (optionally reflected by mirror(s) 41) to the object or workpiece 40 in which ultrasound is propagating. The light scattered off the workpiece 40 surface, which has acquired phase modulation following the ultrasonic motion of the surface, is collected by a lens 30 and sent to the wavefront adaptive photorefractive two-wave mixing demodulator 12. The pump beam and the collected signal beam interfere and write an holographic grating 29 inside the photorefractive crystal 27. The beam from the pump beam diffracted by this grating 29 (reference beam or local oscillator beam) is superimposed on the transmitted signal beam and both interfere to give a signal representative of the ultrasonic motion. If required, a wave plate 32 is used to adjust the quadrature between the signal beam and the diffracted pump beam.

The transmitted signal beam is then detected in a differential detector. It is first separated in two by a polarizing beam splitter 34. Each beam is sent to a photodetector 36 where the reference and the phase-modulated signal beams interfere and give amplitude modulated electrical signals representative of the ultrasonic motion with opposite polarity. The signals from the two detectors are then subtracted in a differential amplifier 38 to substantially eliminate the effect of the intensity fluctuations of the laser oscillator.

The frequency tracking capability of such a scheme and its adapting feature is also a key to its successful application in this case since the frequency of the laser oscillator is not stable especially from shot to shot. Some frequency chirp could also be present during the pulse so strong laser beam for pumping the crystal may be needed. Such a demodulator has been previously described in U.S. Pat. No. 5,131,748 by J. P. Monchalin, R. K. Ing, *Broadband Optical Detection of Transient Motion From a Scattering Surface by Two-Wave Mixing in a Photorefractive Crystal* and in U.S. Pat. No. 5,680,212 by A. Blouin, P. Delaye, D. Drolet, J.-P. Monchalin and G. Roosen, *Sensitive and Fast Response Optical Detection of Transient Motion From a Scattering Surface by Two-Wave Mixing*. However such a demodulator has always been used with stable single frequency lasers as described above and never with a laser source with limited stability and noise figure as the pulsed laser oscillator.

Although FIG. 4 shows direct beam coupling between the laser, the surface and the demodulator, fiber coupling using large core multimode fibers can be used. While not sensitive to intensity fluctuations, the demodulator is usually sensitive to phase noise. The inventors have found that a convenient and practical way to avoid sensitivity to phase fluctuations is to ensure that the pump and signal beam path lengths are substantially equal, and this is conveniently implemented by selecting the proper lengths of optical fibers.

For example, for a given testing setup the optical pathlengths from the laser to the surface and from the surface to the demodulator being set, an optical length of fiber equal to the sum of the two previous path lengths will chosen for transmitting the pump beam.

Figure 8:
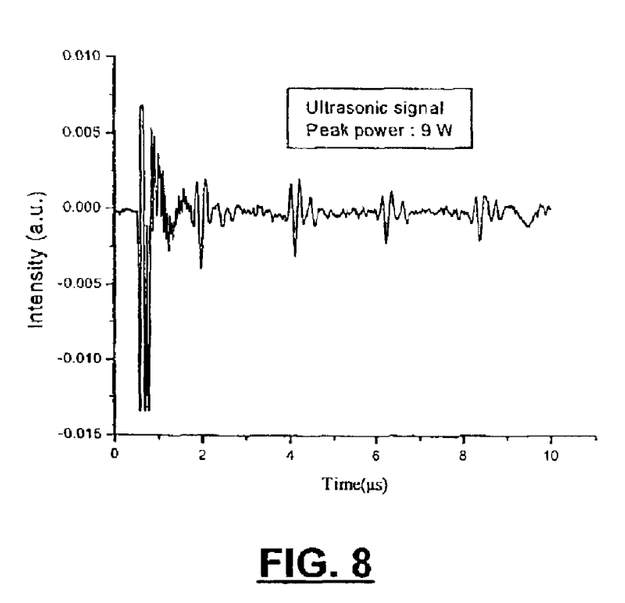
FIG. 8 shows the ultrasonic signal obtained with the laser oscillator in the single frequency mode.

Successful operation of such a detection system is evidenced by the data shown in FIG. 8. FIG. 8 shows a typical ultrasonic signal obtained with the embodiment of FIG. 4, with the laser oscillator operated in the single frequency regime. For this data, ultrasound was generated by a piezoelectric transducer mounted on the opposite surface of a reflecting object. The various ultrasonic echoes are clearly identified. Note that the first peaks correspond to spurious electrical noise from the ultrasonic pulser that could have avoided by better electrical shielding.

Although single frequency operation is preferable for flexibility of use and no severe restriction in the path lengths, detection with a multi-mode laser oscillator, i.e. with a laser with a much shorter coherence length is possible by making the signal beam path and the pump beam path very carefully equal.

FIG. 4 represents the basic embodiment according to the invention. Several variants are possible. First regarding mode selection, the etalon can be replaced by selecting elements outside the laser cavity, such as a Fox and Li mode selector, which is actually a two-wave interferometer. Other external mode selectors making an additional external cavity could also be used. The etalon can also be replaced by a photorefractive crystal inserted in the cavity working as an adaptive mode selector, as described by N. Huot, J. M. Jonathan, G. Pauliat, P. Georges, A. Brun, G. Roosen, *Laser mode manipulation by intracavity dynamic holography: Application to mode selection*, Appl. Phys. B, 69, 155, (1999). The mode selection can also be made by a permanent holographic grating which can also acts as a laser cavity mirror, if the grating reflectivity is large enough.

Other variants concern the phase demodulation part of the embodiment. The two-wave mixing demodulator could be replaced by a photo-emf-based receiver, as proposed by M. P. Petrov, I. A. Sokolov, S. I. Stepanov, G. S. Trofimov in the article cited above. The polarization self-modulation effect as proposed by K. Päivasaari, A. A. Kamshilin in an article cited above could also be used alternatively.

When frequency doubling is used for limiting the power inside the laser oscillator cavity, the frequency doubled beam could be used for ultrasound detection concurrently with a two-wave mixing demodulator and any of the alternatives mentioned above.

Figure 9:
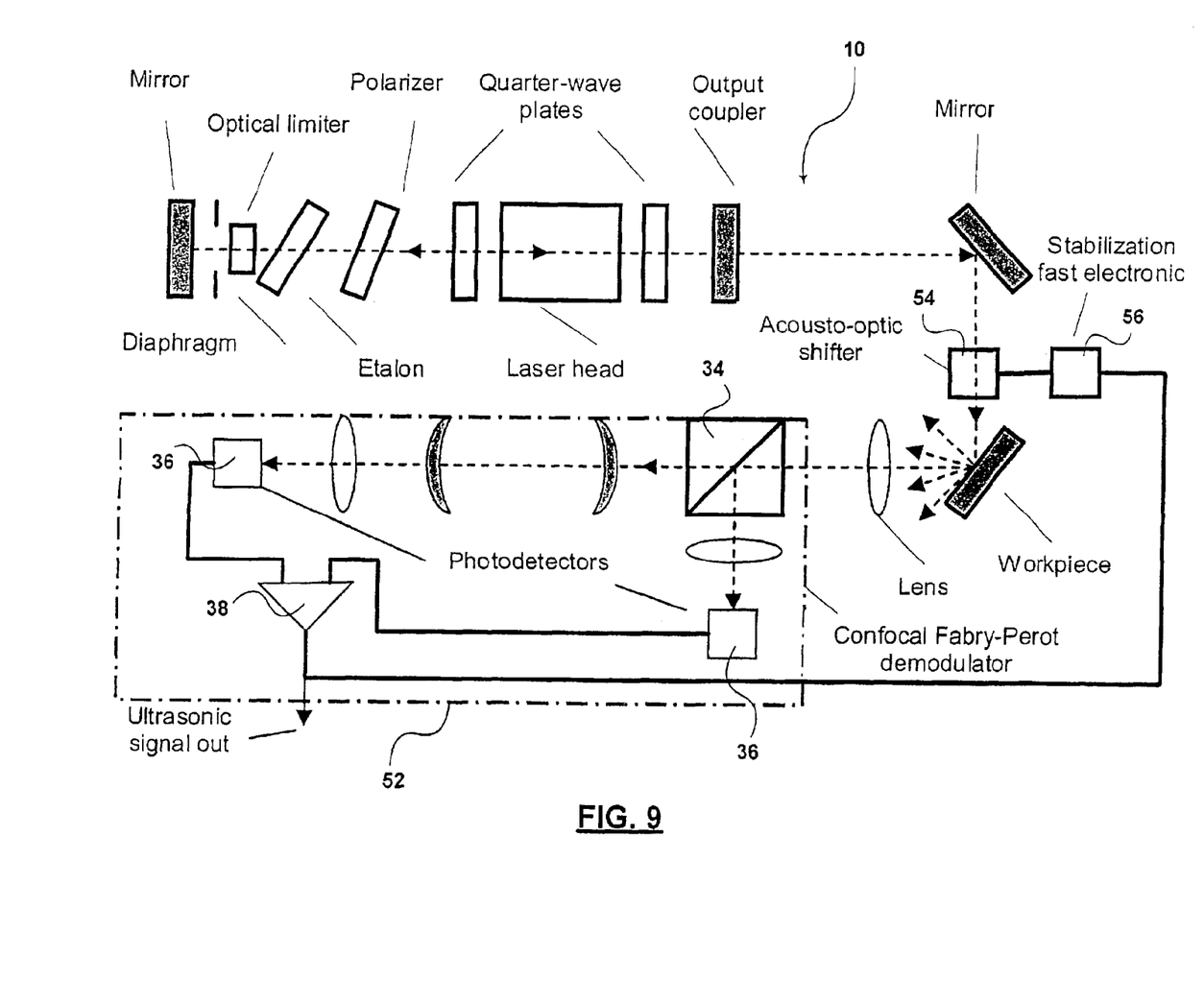
FIG. 9 is a schematic view of a second embodiment of a detection system that includes a pulse laser oscillator coupled to a differential confocal Fabry-Perot demodulator.

FIG. 9 shows an alternate embodiment whereby the pulse laser oscillator 10 operating on a single frequency is used concurrently with a confocal Fabry-Perot demodulator 52. This demodulator has to be insensitive to intensity fluctuations and one version has been described by J.-P Monchalin and R. Héon in U.S. Pat. No. 5,080,491 cited above. FIG. 9 shows a simpler version in which the fluctuations measured at the entrance of the interferometer are subtracted from the output signal with a differential amplifier. This scheme works since the signals at the entrance and at the output are in a given ratio (about 1/4 for detectors of equal sensitivities).

This scheme is not effective for higher frequencies intensity fluctuations and the two-channel confocal Fabry-Perot described in the cited patent has to be used. Tracking to the variations from shot to shot of the laser frequency requires special means. As shown in FIG. 9, this is provided by an acousto-optic frequency shifter 54 and fast electronics 56.

As shown also in FIG. 9 the signals received by the detectors at the entrance and output of the interferometer are measured and compared. If the frequency is not at the proper location, i.e. at about half height of a resonance peak, the ratio of the signals will not be proper and a correction signal will be derived. This correction signal is then applied to the acousto-optic frequency shifter 54 to get the proper frequency value. This being done ultrasound can be detected during the remaining part of the pulse. It should also be noted that as a time-delay interferometer, the confocal Fabry-Perot 52 is more restrictive on the laser stability and coherence length of the laser than the two-beam mixing interferometers in which the pump and signal beam pathlenghts can be made nearly equal. More precisely, the confocal Fabry-Perot requires that the laser coherence length is larger than the product of the Fabry-Perot Finesse by the cavity round trip time.

Figure 10:
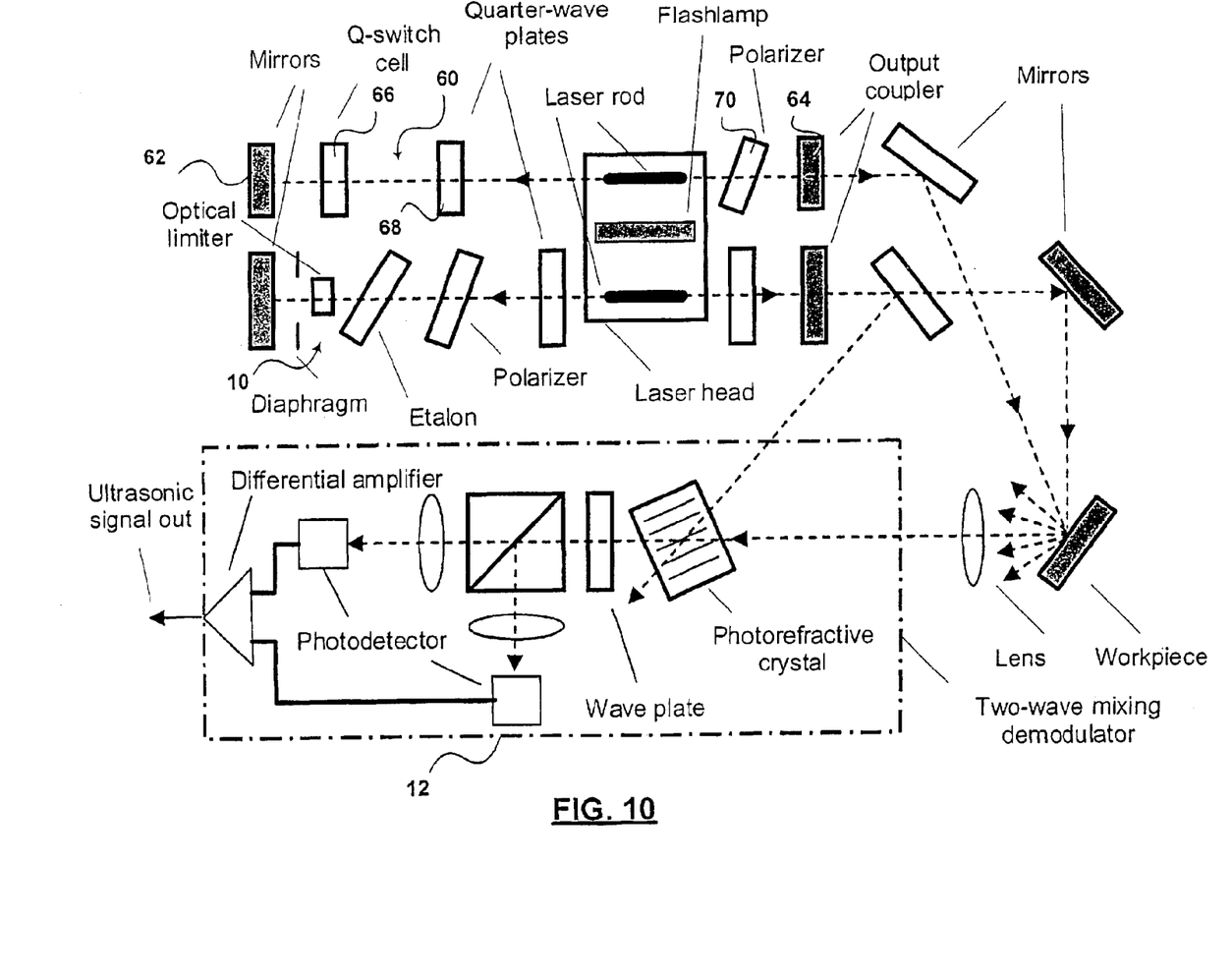
FIG. 10 is a schematic block diagram of a third embodiment that shows an integrated generation-detection laser-ultrasonic system using one flashlamp for optical pumping of both the laser rod of the detection (long-pulse) laser oscillator and the laser rod of the generation (Q-Switched) laser oscillator.

The third embodiment shown in FIG. 10 is obtained by combining two laser rods 63 pumped by the same flashlamp 65, forming preferably a laserhead 18. One laser is the detection pulsed laser oscillator as previously described. The second laser 60 is a standard high power, Q-switched laser and is used for the generation of ultrasound. The generation laser cavity is composed of a mirror 62, and output coupler 64, a Q-switch cell 66, a quarter-wave plate 68 and a polarizer 70.

The output of this laser is sent to the object or workpiece 40 to generate ultrasound that is detected by the detection laser associated with a suitable demodulator such as the two-wave mixing setup described above. The opening of the Q-switch cell is timed in such a way that the time when ultrasound is detected corresponds to the zone where the relaxation oscillations of the detection pulsed laser oscillator have been damped out and noise is minimum. Alternatively, a very simple system can be made by using a single laser slab medium pumped by a flashlamp or a diode array. The path of the detection laser oscillator and of the generation laser oscillator are spatially separated.

The innovative system disclosed is more compact, simpler and cheaper than the currently used scheme while maintaining the high sensitivity required for the industrial applications of laser-ultrasonics.

What we claim is:

1. A method for ultrasonic testing of objects comprising:
   generating ultrasound inside or at the surface of the object;
   providing a long-pulse laser oscillator for generating an incident beam and comprising a resonant cavity containing a lasing medium;
   strongly pumping said lasing medium for a sufficient period of time to generate a laser pulse that during an initial period has a strongly fluctuating intensity and during a subsequent quieter period has an intensity with substantially reduced fluctuations;
   illuminating the surface of the object with said incident beam;
   collecting light from said incident beam that is scattered or reflected by the surface of the object;
   demodulating the light scattered or reflected during said subsequent period of said laser pulse;
   with a frequency tracking demodulator to obtain a signal beam; and
   detecting said signal beam with a differential detector to compensate for residual intensity fluctuations and obtain a signal representative of the ultrasonic motion.

2. A method as claimed in claim 1, wherein the laser oscillator is a single frequency laser.

3. A method as claimed in claim 2, wherein the laser oscillator is made single frequency by employing frequency selective elements inside or outside the laser cavity.

4. A method claimed in claim 1, wherein the laser oscillator is made substantially free of intensity fluctuations by performing intra-cavity frequency conversion in harmonics.

5. A method as claimed in claim 1, wherein the incident beam from the laser oscillator is amplified before being sent onto the surface of the object.

6. A method as claimed in claim 1, wherein the frequency tracking is performed with an electronic stabilization network.

7. A method as claimed in claim 1, wherein the frequency tracking is performed passively by mixing in a non-linear optical element first and second beams, one being directly derived from the laser oscillator and the other being composed of said scattered or reflected light collected from the surface of the object.

8. A method as claimed in claim 7, wherein the optical path lengths from the laser oscillator along said first and second beams are substantially equal.

9. A method as claimed in claim 1, wherein the demodulation is performed independently of the optical speckle present in the light scattered by the surface.

10. A method as claimed in claim 1, wherein the ultrasound generation is generated by another laser.

11. A method as claimed in claim 1, wherein demodulation is performed by two-wave mixing in a photorefractive crystal.

12. A method as claimed in claim 11, wherein a portion of said incident beam is split off and mixed with a beam obtained from said light scattered or reflected off the surface of the object in said photorefractive crystal to form said signal.

13. A method as claimed in claim 12, wherein said detecting of said signal beam with a differential detector is carried out by splitting said signal beam with a polarizing beam splitter into respective polarized beams, directing said respective polarized beams at photodetectors which output amplitude modulated electrical signals representative of the ultrasonic motion with opposite polarity, and passing the outputs of said photodetectors through a differential amplifier to provide said signal representative of the ultrasonic motion.

14. A method as claimed in claim 1, wherein said light is demodulated with a confocal Fabry-Perot demodulator.

15. An apparatus for the ultrasonic testing of an object comprising:

an ultrasound generator for generating ultrasound inside or at the surface of the object;

a long pulse laser oscillator for generating an incident beam for illuminating the surface of the object, said laser oscillator comprising a resonant cavity containing a lasing medium and generating a laser pulse that during an initial period has a strongly fluctuating intensity and during a subsequent quieter period has an intensity with substantially reduced fluctuations;

a light collector for collecting light from said incident beam that is scattered or reflected by the surface of the object;

a frequency tracking demodulator for demodulating the collected light during said subsequent period of the laser pulse to obtain a signal beam; and a differential detector for detecting said signal beam while compensating for residual intensity fluctuations in said incident beam to generate an output signal representative of the ultrasonic motion.

16. An apparatus as claimed in claim 15, wherein the laser oscillator comprises, in a cavity thereof, a limiting aperture to select the $TEM_{00}$ transverse mode, and one or more etalons to select one longitudinal mode.

17. An apparatus as claimed in claim 15, wherein tie laser oscillator further includes a polarization selecting element and a quarter-wave plate on each side of the laser rod to reduce spatial hole burning.

18. An apparatus as claimed in claim 15, wherein the laser oscillator further includes a nonlinear frequency-doubling crystal inserted in the laser cavity to reduce the decay time of the relaxation oscillations of the laser oscillator.

19. An apparatus as claimed in claim 15, wherein the laser oscillator further includes an optical limiter inserted in the laser cavity to reduce the decay time of the relaxation oscillations of the laser oscillator.

20. An apparatus as claimed in claim 15, wherein the laser oscillator comprises, in said cavity, a limiting aperture to select the $TEM_{00}$ transverse mode, and a photorefractive crystal to select one longitudinal mode.

21. An apparatus as claimed in claim 15, wherein the laser oscillator has an electrical power supply providing a pulse sufficiently long and sufficiently intense for relaxation oscillations to be damped out.

22. An apparatus as claimed in claim 15, wherein the laser oscillator comprises, in said cavity, a limiting aperture to select the $TEM_{00}$ transverse mode, and frequency selecting element to select one longitudinal mode.

23. An apparatus as claimed in claim 22, wherein the said frequency selecting element also acts as cavity mirror.

24. An apparatus as claimed in claim 22, wherein the said frequency selecting element is outside the laser cavity.

25. An s as claimed in claim 15, wherein the demodulator includes a non-linear optical element for mixing two beams, one being directly derived from the laser oscillator and the other being composed of said light scattered or reflected by the surface of the object.

26. An apparatus such as claimed in claim 25, wherein the optical path lengths from the laser oscillator along said two beams are substantially equal.

27. An apparatus as claimed in claim 25, wherein the non-linear element is a photorefractive crystal combined with a differential detector.

28. An apparatus claimed in claim 25, wherein the non-linear element is a photo-emf based photoreceiver.

29. An apparatus as claimed in claim 25, wherein the non-linear element is based on the self-modulation of the polarization.

30. An apparatus claimed in clam 15, wherein the demodulator is a differential confocal Fabry-Perot associated with a fast stabilization network allowing rapid stabilization during each laser pulse before demodulation.

31. An apparat as claimed in claim 15, wherein the laser oscillator is pumped by a flashlamp.

32. An apparatus as claimed in claim 15, wherein the laser oscillator includes a rod, a disk or a slab that is pumped by laser diodes.

33. An apparatus such as claimed in claim 15, wherein the ultrasound generator is another laser.

34. An apparatus such as claimed in claim 33, wherein the laser oscillator and said laser for generating ultrasound are pumped by the same optical pump.

35. An apparatus as claimed in claim 34, wherein said optical pump is a flashlamp or diode array.

36. An apparatus as claimed in clam 33, wherein the laser oscillator and said laser for generating ultrasound use a common laser slab medium.

37. An apparatus as claimed in claim 15, wherein said differential detector comprises a polarizing beam splitter for splitting said signal beam into respective polarized beams, a pair of photodetectors for receiving said respective polarized beams which output amplitude modulated electrical signals representative of the ultrasonic motion with opposite polarity, and a differential amplifier to provide said signal representative of the ultrasonic motion.

* * * * *